US009894915B2

(12) United States Patent
Pibarot (10) Patent No.: US 9,894,915 B2
(45) Date of Patent: Feb. 20, 2018

(54) FOOD ANALOGS AND METHODS FOR MAKING FOOD ANALOGS

(75) Inventor: Patrick Pibarot, Guillaucourt (FR)

(73) Assignee: NESTEC SA, Vevey (CH)

( * ) Notice: Subject to any disclaimer, the term of this patent is extended or adjusted under 35 U.S.C. 154(b) by 683 days.

(21) Appl. No.: 13/981,214

(22) PCT Filed: Jan. 24, 2012

(86) PCT No.: PCT/US2012/022306
§ 371 (c)(1),
(2), (4) Date: Sep. 27, 2013

(87) PCT Pub. No.: WO2012/103056
PCT Pub. Date: Aug. 2, 2012

(65) Prior Publication Data
US 2014/0010916 A1      Jan. 9, 2014

Related U.S. Application Data

(60) Provisional application No. 61/461,922, filed on Jan. 25, 2011.

(51) Int. Cl.
| | |
|---|---|
| *A23K 1/10* | (2006.01) |
| *A23K 40/25* | (2016.01) |
| *A23K 40/20* | (2016.01) |
| *A23K 40/30* | (2016.01) |
| *A23K 10/26* | (2016.01) |
| *A23K 50/42* | (2016.01) |
| *A23L 13/40* | (2016.01) |
| *A23L 13/50* | (2016.01) |
| *A23L 13/60* | (2016.01) |

(52) U.S. Cl.
CPC ............... *A23K 1/10* (2013.01); *A23K 10/26* (2016.05); *A23K 40/20* (2016.05); *A23K 40/25* (2016.05); *A23K 40/30* (2016.05); *A23K 50/42* (2016.05); *A23L 13/42* (2016.08); *A23L 13/428* (2016.08); *A23L 13/432* (2016.08); *A23L 13/52* (2016.08); *A23L 13/67* (2016.08)

(58) Field of Classification Search
CPC .......... A23K 1/10; A23K 1/106; A23K 1/004; A23K 1/003; A23K 1/1853; A23K 40/20; A23K 40/25; A23K 40/30; A23K 50/42; A23K 10/26; A23L 1/31409; A23L 1/3177; A23L 1/31463; A23L 1/31445; A23L 1/3152; A23L 13/67; A23L 13/432; A23L 13/52; A23L 13/42; A23L 13/428
See application file for complete search history.

(56) References Cited

U.S. PATENT DOCUMENTS

| | | | | |
|---|---|---|---|---|
| 4,529,359 | A * | 7/1985 | Sloan | E03F 5/22 417/10 |
| 4,606,923 | A * | 8/1986 | Ricke | A21D 13/0083 426/439 |
| 5,456,933 | A * | 10/1995 | Lee | A23K 1/1853 426/516 |
| 6,485,747 | B1 * | 11/2002 | Flanagan | A61K 9/286 424/479 |
| 7,172,776 | B2 * | 2/2007 | Bauer | A21D 13/41 426/128 |
| 2004/0076347 | A1 | 4/2004 | Johnson | |
| 2006/0035003 | A1 * | 2/2006 | McMindes | A23L 1/2005 426/634 |
| 2006/0120975 | A1 | 6/2006 | Scherl et al. | |
| 2006/0260537 | A1 * | 11/2006 | Brent, Jr. | A23K 1/002 117/86 |
| 2009/0208612 | A1 * | 8/2009 | Reiser | A23J 3/18 426/104 |
| 2009/0291188 | A1 * | 11/2009 | Milne | A23L 1/0076 426/574 |
| 2010/0233347 | A1 * | 9/2010 | Uhrhan | A23J 3/227 426/646 |
| 2011/0111102 | A1 * | 5/2011 | Saylock | A23K 1/10 426/240 |

FOREIGN PATENT DOCUMENTS

| | | | |
|---|---|---|---|
| JP | 200178352 A | * | 7/2001 |
| KR | 2005017040 A | * | 2/2005 |

OTHER PUBLICATIONS

Yankellow, Jeff. "What's Rising" from San Fancisco Baking Institute Newsletter, Fall 2003, 12 pages. Downloaded from www.sfbi.com/pdfs/NewsF03.pdf.*
Moncel, Bethany "Yeast Varieties" 2 pages downloaded from http://foodreference.about.com/od/Ingredients_Basics/a/YeastVarieties.htm, dated Mar. 2012.*
"All About Yeast: Active Dry, Instant and Fresh—Allrecipes Dish" downloaded from dish.allrecipes.com/yeast-the-basics/, 8 pages downloaded on Apr. 17, 2017.*
International Search Report & Written Opinion from PCT/US2012/22306, dated May 8, 2012.

* cited by examiner

*Primary Examiner* — Chhaya Sayala (57) ABSTRACT

The invention provides food analogs and methods of making the food analogs. In general, the methods comprise comminuting one or more meats to produce a meat slurry, admixing one or more flours to produce a powder blend, admixing the meat slurry and the powder blend to produce a dough, and extruding the dough at a shear mechanical energy ranging from about 50 kJ/kg to about 500 kJ/kg and at a temperature ranging from about 60° C. to about 120° C. to produce a food analog. Colorant can be added before, during, or after the admixing or extrusion processes to provide a more natural appearance to the food analog. The food analog can be a meat analog having the appearance of a meat or a non-meat food analog such as a fruit or vegetable.

18 Claims, 5 Drawing Sheets

FOOD ANALOGS AND METHODS FOR MAKING FOOD ANALOGS

CROSS REFERENCE TO RELATED APPLICATIONS

This application is a national stage application under 35 USC § 371 of PCT/US2012/022306 filed on 24 Jan. 2012 and claims priority to U.S. Provisional Application No. 61/461,922 filed 25 Jan. 2011, the disclosures of which are incorporated herein by this reference.

BACKGROUND OF THE INVENTION

Field of the Invention

The invention relates generally to food analogs and particularly to food analogs having the appearance of real foods such as meats, vegetables, and fruits and to methods for making such food analogs.

Description of Related Art

Many known food analogs such as dry pet foods are formed in geometrical, regular shaped pieces that do not always have an appearance that represents natural foods such as meats, vegetables, and fruits, e.g., pet food kibbles. Although their textures have a somewhat meaty texture, even soft meaty chunk food analogs may not have the appearance of real meat chunks. Few, if any, dry pet food analogs currently exist that have meat analogs that have a credible meat appearance. There is, therefore, a need for new food analogs that resemble actual food products such as meats, vegetables, and fruits.

SUMMARY OF THE INVENTION

It is, therefore, an object of the invention to provide food analogs that have the appearance of natural foods such as meats, vegetables, and fruits.

It is another object of the invention to provide meat analogs that have the appearance of real meat, e.g., roasted or marinated meat.

It is another object of the invention to provide non-meat analogs that have the appearance of vegetables or fruits, e.g., potatoes or apples.

It is a further object of the invention to provide blended food compositions that contain food analogs of the invention and one or more other comestible ingredients or compositions.

One or more of these or other objects are achieved using methods for making food analogs. The methods comprise comminuting one or more meats to produce a meat slurry, admixing one or more flours to produce a powder blend, admixing the meat slurry and the powder blend to produce a dough, and extruding the dough at a shear mechanical energy ranging from about 50 kJ/kg to about 500 kJ/kg and at a temperature ranging from about 60° C. to about 120° C. The methods produce food analogs having various distinct and unique appearances and textures, e.g., meats and vegetables prepared using various food preparation methods. In some embodiments, one or more colorants are added before, during, or after the admixing or extrusion processes to provide a more natural appearance to the food analog. The food analog can be further processed to form the food analog pieces or other food analog forms. The food analog can be a meat analog or a non-meat food analog such as a fruit or vegetable.

Other and further objects, features, and advantages of the present invention will be readily apparent to those skilled in the art.

DETAILED DESCRIPTION OF THE INVENTION

Definitions

The term "animal" means an animal capable of consuming and benefiting from the food analogs of the invention. For example, animals can refer to pets such as dogs or cats or other animals such as humans, equines, bovines, and porcines.

The term "meat" means meat and meat by-products including carcass, bones, skin, offal, and muscle. Fresh meat may be obtained directly from a slaughterhouse and is often selected from poultry including chicken, turkey, duck and goose; fish including tuna, salmon, trout, and cod; ovines including lamb and sheep; bovines including cow, calf and veal; and porcines including pig and wild pig. In some embodiments, the meat slurry can include ground or emulsified frozen meats.

The term "single package" means that the components of a kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof. A single package may be containers of individual components physically associated such that they are considered a unit for manufacture, distribution, sale, or use.

The term "virtual package" means that the components of a kit are associated by directions on one or more physical or virtual kit components instructing the user how to obtain the other components, e.g., a bag or other container containing one component and directions instructing the user to go to a website, contact a recorded message or a fax-back service, view a visual message, or contact a caregiver or instructor to obtain instructions on how to use the kit or safety or technical information about one or more components of a kit.

As used herein, ranges are used herein in shorthand, so as to avoid having to list and describe each and every value within the range. Any appropriate value within the range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "a food analog" or "a method" includes a plurality of such "food analogs" or "methods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context.

The terms "comprising" or "including" are intended to include embodiments encompassed by the terms "consisting essentially of" and "consisting of". Similarly, the term "consisting essentially of" is intended to include embodiments encompassed by the term "consisting of".

All percentages expressed herein are by total weight of the composition unless specifically stated otherwise. The skilled artisan will appreciate that the term "dry matter basis" means that an ingredient's concentration in a composition is measured after any free moisture in the composition is removed.

The methods and compositions and other advances disclosed here are not limited to particular methodology, protocols, ingredients, components, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

The Invention

In one aspect, the invention provides methods for making food analogs. The methods comprise comminuting one or more meats to produce a meat slurry, admixing one or more flours to produce a powder blend, admixing the meat slurry and the powder blend to produce a dough, and extruding the dough at a shear mechanical energy (ISME) ranging from about 50 kJ/kg to about 500 kJ/kg and at a temperature ranging from about 60° C. to about 120° C. The methods, depending on the ingredients and the particular process conditions used, produce food analogs having various shapes, colors, properties, and appearances. The food analogs can be used as made or can be further processed to produce additional food analogs having various shapes, colors, properties, and appearances. The resulting food analogs can be used as foods for a meal or for any other suitable purpose, e.g., treats, snacks, food blends, and the like.

The meats are any meats suitable for consumption by an animal and for producing for the desired food analogs, e.g., beef, poultry, and pork. Such meats are known to skilled artisans.

The flours are any flours suitable for consumption by an animal and for producing the desired food analogs. Suitable flours include cereal flours such as wheat, wheat gluten, barley, rice, oat, and corn flour; legume flours such as soy and pea flour; and vegetable flours such as potato, arrowroot, and cassava flour. Other such flours are known to skilled artisans.

In certain embodiments, the dough includes from about 0% to 70% by weight of the meat slurry and from about 70% to about 0% by weight of the powder blend.

In various embodiments, the dough includes from about 30% to 70% by weight of the meat slurry and from about 70% to about 30% by weight of the powder blend. In certain embodiments, the dough includes from about 30% to 70% by weight of the meat slurry, including about 35%, 40%, 45%, 50%, 55%, 60%, and 65% by weight. In certain embodiments, the dough includes from about 30% to 70% by weight of the powder blend, including about 35%, 40%, 45%, 50%, 55%, 60%, and 65% by weight.

In various embodiments, the shear mechanical energy used in the methods is from about 50 kJ/kg to about 500 kJ/kg, including about 75, 100, 125, 150, 175, 200, 225, 250, 275, 300, 325, 350, 375, 400, 425, 450, and 475 kJ/kg and any ranges in between. In various embodiments, the extrusion temperature is from about 60° C. to about 120° C., including about 65, 70, 75, 80, 85, 90, 95, 100, 105, 110, and 115° C.

The various ingredients and food analogs are comminuted, admixed, mixed, extruded, cut, sprayed, coated, and otherwise processed using methods and equipment known to skilled artisans. While admixing contemplates combining several ingredients, admixing is defined to include preparing a single ingredient for use in the process, e.g., using one type or meat or one type of flour. Various sprayers, dryers, and the like used in the methods are common and well known to skilled artisans.

In some embodiments, as known to skilled artisans, the moisture content of the dough is adjusted to make dough with a consistency suitable for extrusion, particularly on particular extrusion equipment. Typically, the moisture content is adjusted by adding water using known methods and equipment.

The original shape of the food analog is typically defined by the extruder die shape. In various embodiments, the food analog is further cut into pieces to produce food analog pieces or further processed to produce food analogs having varying properties, e.g., the appearance of a meat, vegetable, or fruit. When cut at the extruder, the length of each piece can be adjusted by adjusting the knives configuration and the knives rotation speed on the extruder.

In various embodiments, one or more colorants are added at any step during or after production of the food analogs to provide a more natural/realistic appearance to the food analog. For example, one or more colorants can be added to the meat slurry to produce colored food analogs. In addition, one or more colorants can be added to the powder blend to produce colored food analogs. Similarly, one or more colorants can be added as part of a base including a vitamin or mineral premix to the meat slurry. In addition, one or more colorants can be added to the admixed meat slurry and powder blend before extruding. For instance, the colorants can be introduced into the extruder. Various combinations of these embodiments can be used to produce a food analog having the desired appearance.

Suitable colorants include FD & C colors, natural colors, titanium dioxide, etc. The amount of colorant(s) to be added can range from about 0.01% to 10% by weight. Preferably, the amount of colorant(s) can range from about 0.5% to about 5% by weight depending on the colorants and the desired food analog to be obtained.

In another aspect, the invention provides food analogs made using the methods of the invention.

In another aspect, the invention provides food analogs. In various embodiments, the food analogs are a range of dry or semi-moist products that have the appearance of a cooked, roasted, or marinated food chunks that are steamed, baked, or grilled. The food analogs in the form of dry or semi-moist chunks have a real meat appearance, texture, and flavor. The food analogs have a high culinary aspect that corresponds to real meat and to various pet food products. In various embodiments, the food analogs correspond to roasted meat recipes such as beef loin cuts, beef round cuts, roast chicken, roast pork cuts, marinated chicken, marinated pork, and the like. In other embodiments, the food analogs have the appearance of various vegetables and fruits.

The food analogs offer a new alternative to known pet food kibbles by providing pets and pet owners dry and semi-moist pet food products that resemble meaty chunks. The food analogs can be mixed together with dry pellets or kibbles as is done for soft meaty chunks or the food analogs may be sold alone as a meat analog for consumption. In other embodiments, the food analogs are combined with other dried foods such as dried vegetables (e.g., carrot, leeks, or beans).

The meat used to make the meat slurry can be any suitable meat such as poultry, beef, pork, and lamb, especially those types of meats suitable for pets. The meat can include any additional parts of an animal, including offal.

The flours can be derived from any suitable fruits or vegetables (e.g., potatoes, squash, zucchini, spinach, radishes, asparagus, tomatoes, cabbage, peas, carrots, spinach, corn, green beans, lima beans, broccoli, brussel sprouts, cauliflower, celery, cucumbers, turnips, yams, etc.) or grains (e.g., barley, rice, wild rice, brown rice, oats, millet, etc.). The flour can include any suitable spices (e.g., parsley, scallions, sage, rosemary, basil, thyme, chives, etc.) as desired to achieve the final food analog.

In some embodiments, the invention provides food analogs that are meat analogs and the colorants are: (1) azorubine to produce a colored meat analog having a dark red appearance, (2) paprika oleoresin to product a colored meat analog having a light red appearance, (3) a combination of titanium dioxide, allura red, and xanthene to produce a colored meat analog having a pink appearance, (4) a combination of titanium dioxide and xanthene to produce a colored meat analog having a white appearance, (5) a combination of poultry fat, plasma powder, xylose, and sodium monoglutamate to produce a colored meat analog having a dark brown appearance, or (6) a combination of dried egg yolk, caramel color, and starch to produce a colored meat analog having a light brown appearance. Depending on the type and amount of colorant, the meat analog can have an appearance similar to different types of cooked meat such as poultry, beef, or pork. In another embodiment, the colorant is titanium dioxide to produce a food analog having the appearance of fish.

In other embodiments, the invention provides food analogs that are non-meat food analogs and the colorants are: (1) a combination of canthaxanthin and xanthene to produce a non-meat food analog having an orange appearance, (2) a combination of dried egg yolk and tartrazine to produce a non-meat food analog having a yellow appearance, (3) a combination of titanium dioxide and riboflavine to produce a non-meat food analog having a light yellow appearance, (4) a combination of sodium copper chlorophyllin and titanium dioxide to produce a non-meat food analog having a pale green appearance, or (5) a combination of tartrazine, indigo carmine, and nitrited salt to produce a non-meat food analog having a green appearance. Depending on the type and amount of colorant, the non-meat food analog can have an appearance similar to a fruit or vegetable, e.g., potatoes, zucchini, apples, carrots, eggplant, and peppers.

In various embodiments, the food analogs (with or without colorant added during the methods) further include one or more colorants added to the food analogs after extrusion to produce colorant coated food analogs. For example, after extrusion, a solution containing colorants and/or Maillard reaction precursors and/or meat/culinary flavour and/or ground meat dry powder can be sprayed on the food analog to obtain a heterogeneous roasted or marinated coloration as well as an appropriate flavor.

The colorants are added to the food analog using any suitable application technique such as, for example, spraying, dipping, enrobing, panning, and the like. Spraying may be done in a continuous tumbler (e.g., post extrusion coating). Alternatively, or in addition to, a powder dusting system can heterogeneously stick some colored or reactive powders on the top the food analog after the post extrusion coating to improve the roasted appearance of the food analog.

In various embodiments, the colorant coated food analog can be cut to produce cut colorant coated food analog pieces. The cut colorant coated food analog pieces can be dried to further improve the appearance of the colored food analog pieces.

In an alternative embodiment, the colorant coated food analog can first be dried. After drying, the dried colorant coated food analog can then be cut to produce colored food analog pieces.

The colorants added to the food analogs after extrusion are generally the same colorants added to the meat slurry, powder blend, meat slurry and powder blend admixture, and other ingredients before or during extrusion. The resulting food analogs are the same as very similar to the food analogs produced when the colorants are added before or during extrusion.

In other embodiments, one or more leavening agents are added or injected into the dough, preferably in the extruder. If no leavening agents are added, the shape given by the die can be kept up to the end of the process, and the food analog may be elastic and rigid. If a leavening agent is injected in the extruder, the food analog can become puffed during the drying step. The initial shape of the food analog can change and more randomly distributed shapes are created giving more natural, less industrial chunky shapes. Furthermore, the puffed food analog's texture can become more aerated and flexible while retaining elasticity.

The leavening agent can be injected into the dough, preferably in the extruder, to obtain puffed chunks of the food analog after extruding, drying and cooling. In an embodiment, the leavening agent is yeast. Alternatively, the leavening agent can be one or more of beer (e.g., unpasteurizedlive yeast), buttermilk, ginger beer, kefir, sourdough starter, yogurt, baking powder, baking soda (e.g., sodium bicarbonate), monocalcium phosphate, sodium aluminum phosphate ("SALP"), sodium acid pyrophosphate ("SAPP"), phosphates, ammonium bicarbonate (e.g., hartshorn, horn salt, bakers ammonia), potassium bicarbonate (e.g., potash), potassium bitartrate (e.g., cream of tartar), potassium carbonate (e.g., pearlash), hydrogen peroxide, nitrous oxide or a combination thereof.

The food analogs may include other suitable ingredients such as, for example, preservatives, oral care ingredients, humectants, antioxidants, vitamins, minerals, or a combination thereof in any suitable amounts. The additional ingredients can further by using to promote a healthy lifestyle of an animal. The ingredients can be added at any suitable point during the food analog manufacturing process.

The food analogs may also include one or more polyols (e.g., mono-propylene glycol or glycerol) or salt to lower the water activity of the finished product as well as preservatives to prevent mold growth. Suitable examples of preservatives include potassium sorbate, sorbic acid, methyl para-hydroxybenzoate, calcium propionate and propionic acid.

The oral care ingredients can provide breath freshening and/or tartar control. Suitable oral care ingredients include alfalfa nutrient concentrate (contains chlorophyll), sodium bicarbonate, phosphates (e.g., tricalcium phosphate, acid pyrophosphates, tetrasodium pyrophosphate, metaphosphates, orthophosphates), peppermint, cloves, parsley, ginger, etc.

Suitable humectants include salt, sugars, propylene glycol and polyhydric glycols such as glycerin and sorbitol, and the like. Suitable antioxidants include butylated hydroxyanisole ("BHA") and butylated hydroxytoluene ("BHT"), vitamin E (tocopherols), etc.

Suitable vitamins may include Vitamins A, B-complex (such as B-1, B-2, B-6 and B-12), C, D, E and K, niacin and acid vitamins such as pantothenic acid and folic acid and biotin. Suitable minerals may include calcium, iron, zinc, magnesium, iodine, copper, phosphorus, manganese, potassium, chromium, molybdenum, selenium, nickel, tin, silicon, vanadium, and boron.

In another aspect, the invention provides meat analogs in the form of meat analogs including one or more meats, one or more flours, and one or more colorants. The colorant(s) can be: (1) azorubine to produce a colored meat analog having a dark red appearance, e.g., the appearance of roasted beef or barbeque beef, (2) paprika oleoresin to product a colored meat analog having a light red appearance, e.g., the appearance of cooked meat, roasted veal, roasted pork, marinated veal, or marinated pork, (3) a combination of titanium dioxide, allura red, and xanthene to produce a colored meat analog having a pink appearance, e.g., the appearance of cooked fish, roasted fish, salmon, or marinated fish, (4) a combination of titanium dioxide and xanthene to produce a colored meat analog having a white appearance, e.g., the appearance of lobster, shrimp, or fresh fish, (5) a combination of poultry fat, plasma powder, xylose, and sodium monoglutamate to produce a colored meat analog having a dark brown appearance, e.g., the appearance of roasted or marinated poultry, beef, veal, or pork liver, (6) a combination of titanium dioxide and riboflavine to produce a non-meat food analog having a light yellow appearance, e.g., the appearance of roasted chicken, roasted turkey, or barbeque chicken, or (7) a combination of dried egg yolk, caramel color, and starch to produce a colored meat analog having a light brown appearance, e.g., the appearance of marinated oven cooked beef.

Any of the color combinations described herein for the meat analogs can also be used to provide non-meat food analogs based on the type, amount, or concentration of the added colors. For example, besides a meat analog, a combination of titanium dioxide and xanthene can be used to produce a colored non-meat food analog having a white appearance such as bread, cooked bread, or roasted bread. A combination of dried egg yolk, caramel color, and starch can be used to produce a colored non-meat food analog having a light brown appearance such as a biscuit.

In another aspect, the invention provides non-meat food analogs in the form of food analogs including one or more meats, one or more flours, and one or more colorants. The colorant(s) can be: (1) a combination of canthaxanthin and xanthene to produce a non-meat food analog having an orange appearance, e.g., the appearance of cooked carrot or roasted carrot, (2) a combination of dried egg yolk and tartrazine to produce a non-meat food analog having a yellow appearance, (3) a combination of sodium copper chlorophyllin and titanium dioxide to produce a non-meat food analog having a pale green appearance, e.g., the appearance of roasted apple slices, green vegetable, zucchini, roasted zucchini, or roasted egg plant, or (4) a combination of tartrazine, indigo carmine, and nitrited salt to produce a non-meat food analog having a green appearance, e.g., the appearance of roasted green bell pepper.

In another aspect, the invention provides kits containing the food analogs described herein. The kits include in separate containers in a single package or in separate containers in a virtual package, as appropriate for the kit component, (A) one or more of the food analogs of the invention and (B) one or more of (1) a food sauce to be used in conjunction with the food analog, (2) dry pet food pellets to be used in conjunction with the food analog; (3) dried vegetables to be used in conjunction with the food analog; (4) a picture of an actual food that the food analog is representative of, (5) instructions for how to serve the food analog, (6) a serving apparatus (e.g., bowl, platter, etc.) for serving the food analog, or (7) a serving utensil (e.g., scoop, spoon, etc.) for serving the food analog.

When the kit comprises a virtual package, the kit can be limited to instructions in a virtual environment in combination with one or more physical kit components. The kits may contain the kit components in any of various combinations and/or mixtures. For example, in one embodiment, the kit contains a package containing the food analog and a food sauce to be administered in conjunction with the food analog. In another embodiment, the kit contains a package containing the meat analog and a serving apparatus.

In another aspect, the invention provides a means for communicating information about or instructions for using the food analogs described herein for one or more of (1) administering the food analogs to an animal, (2) describing the food analogs to a pet owner, (3) promoting the health or wellness of an animal, (4) combining the food analogs with other pet foods, or (5) combining the food analogs with other food sauces.

The communication means can be a document, digital storage media, optical storage media, audio presentation, or visual display containing the information or instructions. More specifically, the means can be a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, or any combination thereof. The communication means is useful for instructing on the types and benefits the food and meat analogs described herein.

In another aspect, the invention provides an animal food package including a container and a plurality of food analogs stored within the container. Any one or more of the food analogs described herein can be included in the container. The package can further include a label affixed to the package containing a word or words, picture, design, acronym, slogan, phrase, or other device, or combination thereof, that indicates that the contents of the package contains the food analogs (e.g., information about the food analogs and/or its nutritional or related properties).

Typically, such label or device can include the words "food analog" or "meat analog" or an equivalent expression printed on the packaged describing the type of food that the analog represents. Any package or packaging material suitable for containing food analogs is useful in the invention, e.g., a bag, box, bottle, can, pouch, and the like manufactured from paper, plastic, foil, metal, and the like.

In another aspect, the invention provides a package useful for containing food analogs of the invention. The package comprises at least one material suitable for containing the food analog and a label affixed to the material containing a word or words, picture, design, acronym, slogan, phrase, or other device, or combination thereof, that indicates that the package contains the food analog. Typically, such device comprises the words "real meat appearance" or "food analog having the appearance real meat" or "roasted meat food analog" or "real turkey appearance" or an equivalent expression printed on the material. Any package configuration and packaging material suitable for containing the food analog are useful in the invention, e.g., a bag, box, bottle, can, pouch, and the like manufactured from paper, plastic, foil, metal, and the like. In preferred embodiments, the package further comprises a food analog of the invention. In various embodiments, the package further comprises at least one window that permit the package contents to be viewed without opening the package. In some embodiments, the window is a transparent portion of the packaging material. In others, the window is a missing portion of the packaging material.

In another aspect, the invention provides blended food compositions comprising (1) one or more food analogs of the invention and (2) one or more other comestible ingredients or compositions. The comestible ingredients or compositions can be any comestible ingredient or composition compatible with the food analogs of the invention. Preferably, the comestible composition is one or more dry kibbles suitable for consumption by companion animals, preferably dogs and cats. The comestible composition may be selected from the group consisting of extruded kibbles, baked kibbles, extruded treats, and baked treats. In some embodiments, the comestible ingredient or composition is real meat pieces, preferably in the form of real meat chunks.

The blended food compositions of the invention comprise any suitable amount of one or more food analogs of the invention. Generally, the blended food compositions comprise from about 1 to about 99% for the food analogs, preferably from about 5 to about 99%, most preferably from about 5 to about 95%. In various embodiments, the blended food compositions contain about 20%, 30%, 40%, 50%, 60%, 70%, or 80% food analogs.

In one embodiment, the blended food compositions are formulated to provide "complete and balanced" nutrition for an animal, preferably a companion animal, according to standards established by the Association of American Feed Control Officials (AAFCO). In another embodiment, the food composition is a pet food composition.

EXAMPLES

The invention can be further illustrated by the following examples, although it will be understood that these examples are included merely for purposes of illustration and are not intended to limit the scope of the invention unless otherwise specifically indicated.

Methods

All extrusion was conducted at a temperature below 100° C. and with a minimum shear mechanical energy ("SME") of 50 kJ/kg and maximum SME of 500 kJ/kg. A spray in a roller tumbler was used for post extrusion coating. M-Diccer equipment (rotating knives) was used for post coloring cutting.

Product Specifications

Generally, the products produced in the Examples had a composition of:

| | |
|---|---|
| Moisture | 12 and 19% |
| Water activity | 0.6 to 0.8 |
| Protein | 50 to 60%. (The protein was composed of about 50/50 percent of vegetable and animal proteins) |
| Fat | 6 to 10% (Exclusive of any fat used as a coating) |
| Carbohydrate | Less than 30% |

Example 1

A product was made that had a wheat gluten concentration of 45% w/w. The product expanded after drying and collapsed upon cooling to form a product with a wrinkled surface. The following procedures were used to make the product.

Making a Slurry

Meat emulsion products were produced using the ingredients shown in Table 1. The real meat and/or meat by-products were ground using a grinder equipped with a 1 cm grinding plate and emulsified using an emulsification mill. The other ingredients were mixed into the emulsified meat to produce a homogeneous slurry.

TABLE 1

| Ingredient | Kg | % |
|---|---|---|
| Chicken carcasses | 155 | 24.8 |
| Pork lungs with trachea | 82.5 | 13.2 |
| Turkey skin frozen | 6 | 1.0 |
| Liver frozen | 144 | 23.0 |
| Fish frames | 94 | 15.0 |
| Chicken/pork greaves meal | 14 | 2.2 |
| Calcium carbonate | 21.5 | 3.4 |
| Salt | 15 | 2.4 |
| Glucose syrup | 2.5 | 0.4 |
| Titanium oxide | 5 | 0.8 |
| Red color | 0.06 | 0.0 |
| Choline chloride | 1.6 | 0.3 |
| Glycine | 6 | 1.0 |
| Vitamin + mineral premix | 7.5 | 1.2 |

TABLE 1-continued

| Ingredient | Kg | % |
|---|---|---|
| Mono propylene glycol | 65 | 10.4 |
| Sugar crystal | 5.8 | 0.9 |
| Total | 625.46 | 100.0 |

Making a Powder Blend

The ingredients listed in Table 2 were mixed together in a powder blender and then transferred in a tank.

TABLE 2

|  | Kg | % w/w |
|---|---|---|
| Wheat gluten | 481 | 96.2 |
| Calcium propionate | 4.5 | 0.9 |
| Potassium sorbate | 14.5 | 2.9 |
| Total | 500 | 100 |

Making a Yeast Solution

Alive yeasts as the ones used for bread leavening were dispersed in water at the proportion of about 10 to 20% and left at ambient temperature at least 30 minutes before injection in the process.

Making Coloring Solutions for Injection in the Extruder

Natural or synthetic color blend were diluted in water with or without the addition of gums hydrocolloids to produce coloring solutions. Composition and dosing were adjusted depending on the color hue targeted. The solution can be injected in the extruder to produce colored extrudates. One example of a with yellowish colored solution was given in Table 3 (chicken meat color)

TABLE 3

|  | Kg | % w/w |
|---|---|---|
| Water | 18.97 | 94.85 |
| Titanium dioxide | 0.6 | 3 |
| Xanthane | 0.03 | 0.15 |
| Iron oxide yellow | 0.2 | 1 |
| Corn colorant | 0.2 | 1 |
| Total | 20 | 2 |

Extruding the Composition

The powder mixture was fed to extruder and the meat slurry was pumped for injection in the first barrels of the extruder. The mixture was heated using extrusion to a temperature of about 70 to 90° C. and extruded to produce food composition pieces. Yeast solution as well as color solution were injected in the extruder. The extrusion was run in the condition described in Table 4.

TABLE 4

|  | Kg/h | % w/w |
|---|---|---|
| Meat slurry | 47.5 | 47.5 |
| Powder blend | 47.5 | 47.5 |
| Yeast solution | 2 | 2 |
| Coloring solution | 3 | 3 |
| Total | 100 | 100 |

The screw profile was chosen to produce enough shear mechanical energy (100 to 500 kJ/kg) to obtain an elastic consistent extrudate. The extrudate was cut into pieces at the exit of the extrusion die. The food piece dimensions were about 0.8×0.8 inch (2×2 cm).

Making a Coloring Solution for Post Extrusion Coating

The ingredients listed Table 5 were mixed in a water solution to produce a brown colored solution.

TABLE 5

|  | Kg | % w/w |
|---|---|---|
| Water | 19.60 | 98 |
| Brown color mix | 0.17 | 0.85 |
| Allura red | 0.13 | 0.65 |
| Xanthane | 0.03 | 0.15 |
| Chicken flavor | 0.07 | 0.35 |
| Total | 20 | 100 |

Coating the Extruded Pieces

The extrudate pieces were transported in a rotating tumbler in which the coloring solution was injected and sprayed on the surface of the pellets. The coloring solution injection flow was adjusted to obtain a coloring coating of approx 1%. The spray flow was irregular (pulsating compressed air injection) to produce an irregular and more natural like coloring of the extrudate pieces.

Drying the Colored Extrudate Pieces

At the exit of the tumbler coater, the extrudate pieces were transported to the dryer. The pieces were dried at 130° C. during 15 to 30 minutes to obtain colored kibble with the aspect of grilled chicken meat pieces. The texture of the kibbles was soft and elastic. Kibble moisture was of about 16% and water activity of about 0.70.

Making Slices of Colored Kibbles

Figure 1:
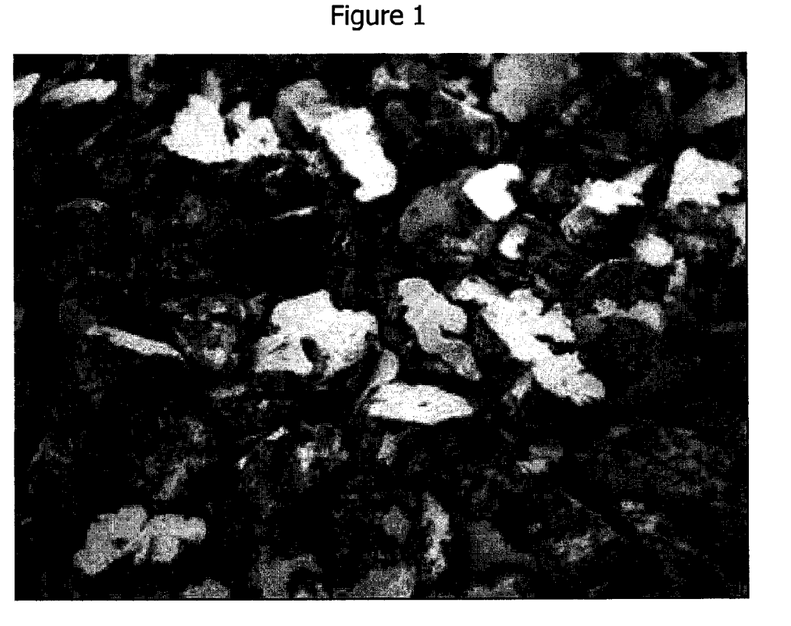
FIG. 1 is a photograph of a meat analog in a first embodiment.

The colored kibble were then cut in a rotary knives cutter in a way to make slice of approx 0.1 to 0.1 inch (0.3 to 0.5 cm) of thickness and a diameter of approx 0.8 inch (2 cm). As shown in FIG. 1, the final product has the appearance of grilled and minced chicken meat, Example 2

Figure 2:
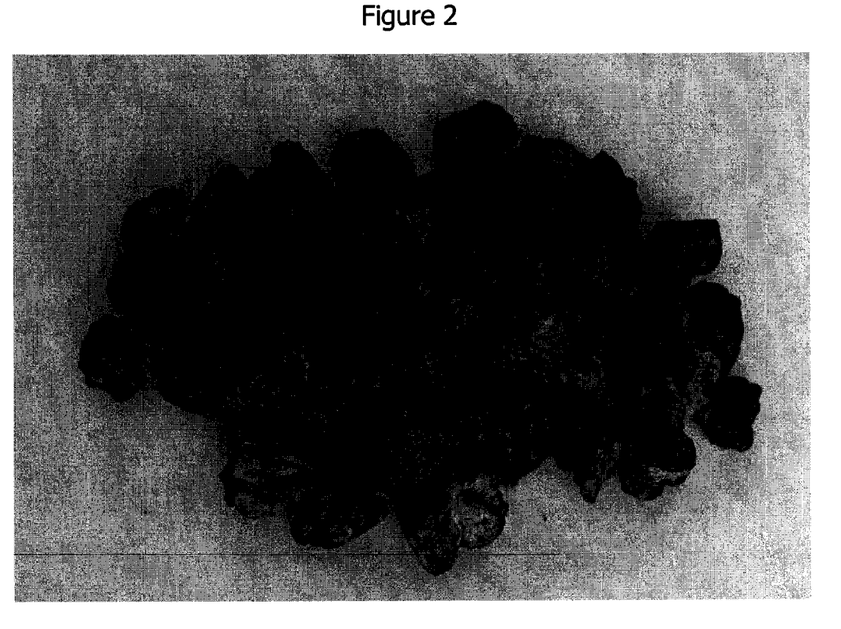
FIG. 2 is a photograph of a meat analog in a second embodiment.

Example 1 was repeated except that the drier cutting step was omitted. As shown in FIG. 2, the resulting product was in the form of kibble with wrinkled surface and had the appearance of roasted meat.

Example 3

Example 1 was repeated except that the yeast and powder blend used was replaced with the blend shown in Table 6.

TABLE 6

|  | Kg | % w/w |
|---|---|---|
| Wheat gluten | 45 | 45 |
| Wheat flour | 30 | 30 |
| Soya flour | 19.5 | 19.5 |
| Distilled monoglyceride | 0.5 | 0.5 |
| Calcium propionate | 2.5 | 2.5 |
| Potassium sorbate | 2.5 | 2.5 |
| Total | 100 | 100 |

Example 4

Example 3 was repeated except that the meat slurry was replaced by the composition given in Table 7.

TABLE 7

| Ingredient name | Kg | % |
|---|---|---|
| Poultry mechanically deboned meat | 122 | 27.1 |
| Frozen Turkey skin | 20 | 4.4 |
| Frozen beef liver | 160 | 35.6 |
| Anchoy surimi | 38 | 8.4 |
| Salt | 13 | 2.9 |
| Glucose | 10.8 | 2.4 |
| Titanium dioxide | 5.5 | 1.2 |
| choline chloride | 1.7 | 0.4 |
| Glycine | 5.5 | 1.2 |
| Vitamin & mineral premix | 6.7 | 1.5 |
| Monopropylene glycol | 57 | 12.7 |
| Crystal sugar | 9.8 | 2.2 |
| Total | 450 | 100.0 |

Figure 3:
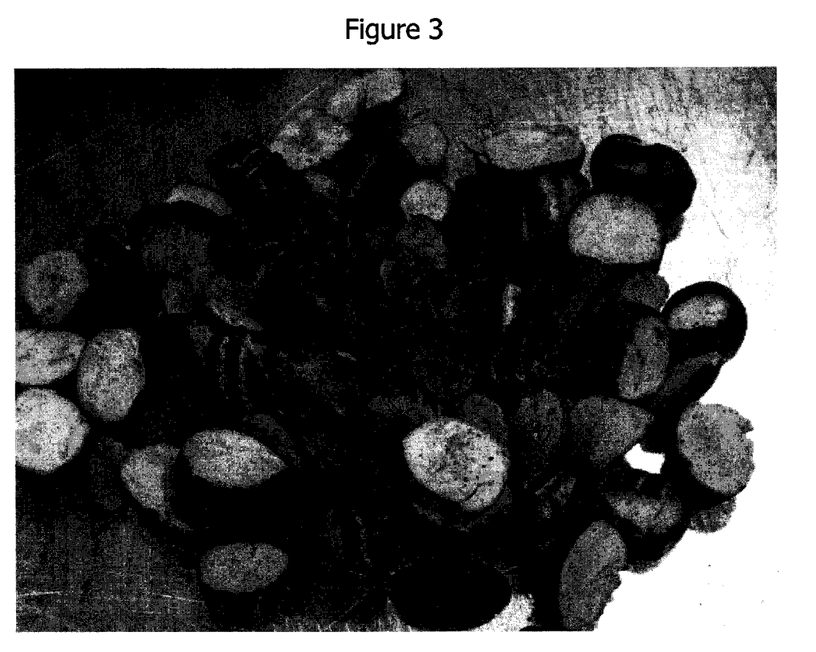
FIG. 3 is a photograph of a meat analog in a third embodiment.

As shown in FIG. 3, the product produced in Example 3 and Example 4 was in the form of a round kibble presenting a colored surface with strips as if the meaty preparation was cooked on a grill. The obtained texture of the inside of the sliced kibble is elastic and cellular like bread texture. The products had a unique appearance and texture. The appearance of the cut kibbles gives the perception of a sliced piece of toasted or roasted bread (crouton).

Example 5

Example 4 was repeated except that the kibbles were not cut after drying. The brown color solution for post extrusion coating is replaced by the following composition

TABLE 8

|  | Kg | % w/w |
|---|---|---|
| Water | 19.60 | 98 |
| Brown color mix | 0.17 | 0.85 |
| Allura red | 0.13 | 0.65 |
| Xanthane | 0.03 | 0.15 |
| Smoked flavor | 0.07 | 0.35 |
| Total | 20 | 100 |

Figure 4:
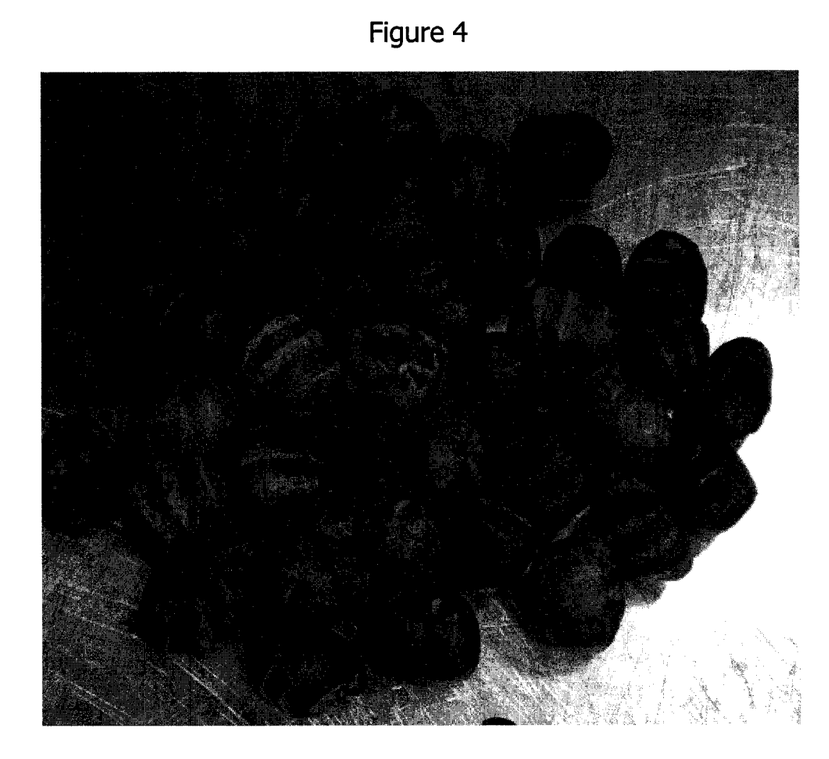
FIG. 4 is a photograph of a meat analog in a fourth embodiment.

As shown in FIG. 4, the product had the appearance of roasted and grilled sausage. The surface of the kibbles and the color may give the perception of roasted small frankfurter.

Example 6

Figure 5:
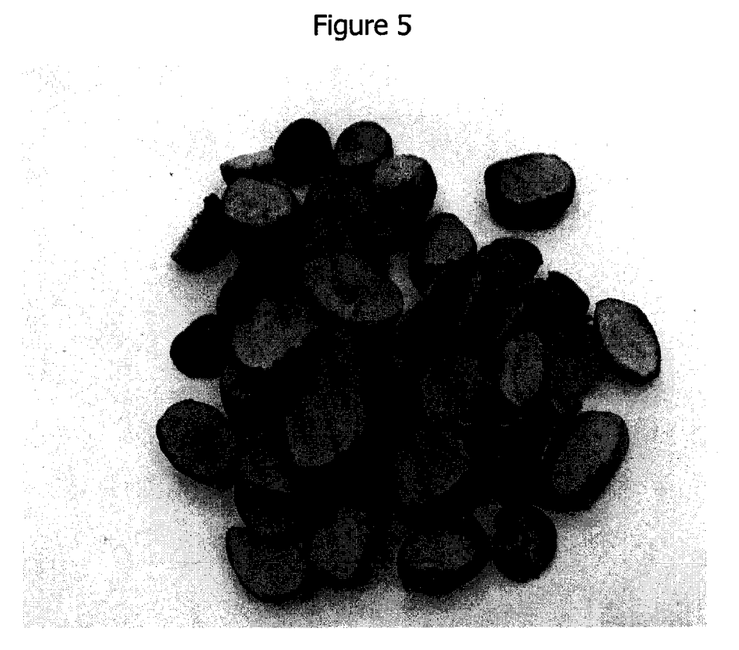
FIG. 5 is a photograph of a meat analog in a fifth embodiment.

Example 4 was repeated except that the colored solution for post extrusion cooking was replaced by the formula given in Table 9 As shown in FIG. 5, the resulting product was in the form of kibble and had a dark color and the appearance of barbequed meat.

TABLE 9

|  | Kg | % w/w |
|---|---|---|
| Poultry fat | 16.9 | 84.5 |
| Plasma powder | 2 | 10 |
| Xylose | 0.5 | 2.5 |
| Sodium monoglutamate | 0.5 | 2.5 |
| Chicken flavor | 0.1 | 0.5 |
| Total | 20 | 100 |

Example 7

Figure 6:
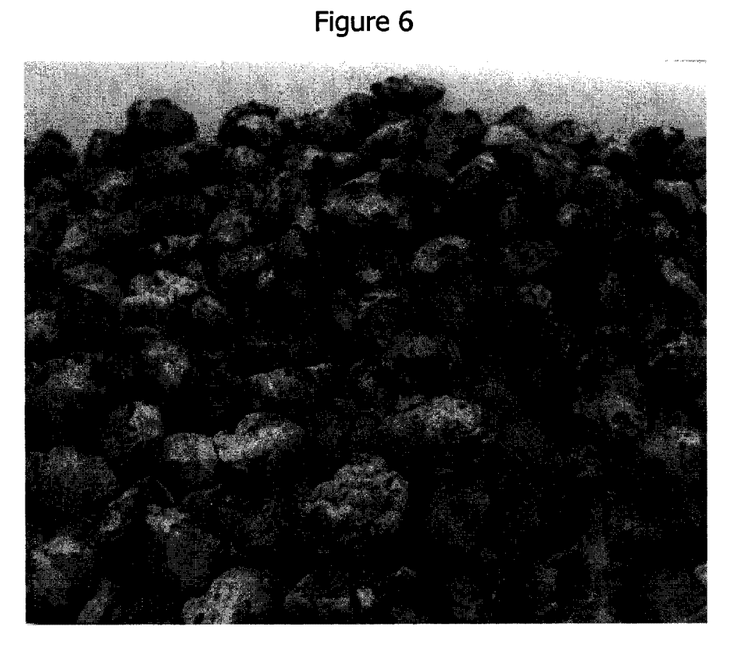
FIG. 6 is a photograph of a meat analog in a sixth embodiment.

Example 5 was repeated except that the extrudate pieces were cut in small pieces of approx 0.3×0.3 inch (0.8×0.8 cm) and coated after extrusion with a solution of liquid caramel diluted in water (1 part of liquid concentrate caramel color in 9 part of pure water). As shown in FIG. 6, the resulting product was in the form of kibble and had the appearance of cooked chicken nuggets.

Example 8

Figure 7:
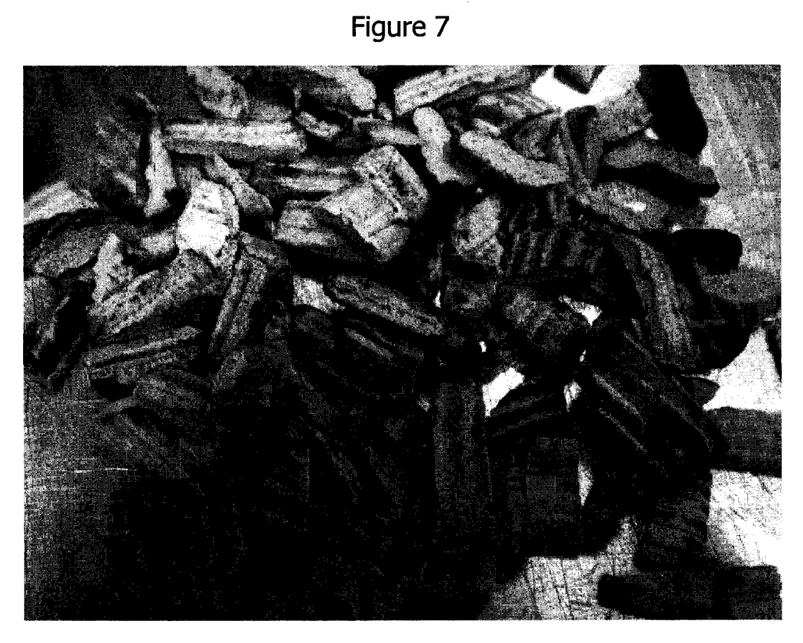
FIG. 7 is a photograph of a meat analog in a seventh embodiment.

Example 1 was repeated except that the extrusion was run with a die with the shape of 1 cm length and 0.2 cm gap with a specific shape to give a "wavy" surface and except that a yeast solution was not used. Furthermore, the solution for injection in the extruder was replaced by the composition given in Table 10. The resulting kibbles were coated with the composition of Table 11 after the composition was diluted by a factor of 20. As shown in FIG. 7, the product was relatively white on the inside and had the appearance of sliced roasted fish.

TABLE 10

|  | Kg | % w/w |
|---|---|---|
| Water | 9.35 | 93.5 |
| TiO$_2$ | 0.5 | 5 |
| Xanthane | 0.15 | 1.5 |
| Total | 10 | 100 |

TABLE 11

|  | Kg | % w/w |
|---|---|---|
| Water | 7.5 | 98 |
| Dark color mix | 1 | 0.85 |
| Sodium glutamate | 0.5 | 0.65 |
| Xanthane | 0.03 | 0.15 |
| Xylose | 0.5 |  |
| Smoke grill flavor | 0.07 | 0.35 |
| Total | 10 | 100 |

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims the invention may be practiced otherwise than as specifically described.

What is claimed is:

1. A method for making a food analog, the method comprising:
   comminuting one or more meats to produce a meat slurry;
   admixing one or more flours to produce a powder blend;
   admixing the meat slurry and the powder blend to produce a dough; and
   injecting live yeast into the dough while extruding the dough at a shear mechanical energy ranging from about 50 kJ/kg to about 500 kJ/kg and at a temperature ranging from about 60° C. to about 120° C. to produce the food analog, and the live yeast is 0.2 wt. % to 0.4 wt. % of the food analog.

2. The method of claim 1 further comprising cutting the food analog into pieces to produce food analog pieces.

3. The method of claim 1 further comprising adding one or more colorants to the meat slurry, and the food analog is a colored food analog.

4. The method of claim 1 further comprising adding one or more colorants to the powder blend, and the food analog is a colored food analog.

5. The method of claim 1 further comprising adding one or more colorants to the admixed meat slurry and the powder blend, and the food analog is a colored food analog.

6. The method of claim 5 wherein the one or more colorants are added to the dough while extruding the dough.

7. The method of claim 1 further comprising adding one or more colorants to a component selected from the group consisting of the meat slurry, the powder blend, the admixed meat slurry, and a combination thereof, and the food analog is a colored food analog.

8. The method of claim 7 wherein the food analog is a meat analog, and at least one of the one or more colorants is selected from the group consisting of: (1) azorubine to produce a colored meat analog having a dark red appearance; (2) paprika oleoresin to produce a colored meat analog having a light red appearance; (3) a combination of titanium dioxide, allura red, and xanthane to produce a colored meat analog having a pink appearance; (4) a combination of titanium dioxide and xanthane to produce a colored meat analog having, a white appearance; (5) a combination of a poultry fat, plasma powder, xylose, and sodium monoglutamate to produce a colored meat analog having a dark brown appearance; and (6) a combination of dried egg yolk, caramel color, and starch to produce a colored meat analog having a light brown appearance.

9. The method of claim 2 wherein:
   the food analog pieces have the shape and the color of pieces of a fruit or vegetable selected from the group consisting of potatoes, zucchini, apples, carrots, eggplant, and peppers,
   the method further comprises adding one or more colorants to a component selected from the group consisting of the meat slurry, the powder blend, the admixed meat slurry, and combinations thereof, and the food analog is a colored food analog, and
   at least one of the one or more colorants is selected from the group consisting of: (1) a combination of canthaxanthin and xanthene to produce a food analog having an orange appearance; (2) a combination of dried egg yolk and tartrazine to produce a food analog having a yellow appearance; (3) a combination of titanium dioxide and riboflavine to produce a food analog having a light yellow appearance; (4) a combination of sodium copper chlorophyllin and titanium dioxide to produce a food analog having a pale green appearance; and (5) a combination of tartrazine, indigo carmine, and nitrited salt to produce a food analog having a green appearance.

10. The method of claim 7 wherein the colorant is titanium dioxide, and the food analog pieces have the color and shape of pieces of fish.

11. The method of claim 1 further comprising applying one or more colorants to the food analog after extrusion to produce a colorant coated food analog.

12. The method of claim 11 further comprising cutting the colorant coated food analog to produce cut colorant coated food analog pieces.

13. The method of claim 12 further comprising drying the cut colorant coated food analog pieces.

14. The method of claim 11 further comprising drying the colorant coated food analog to produce a dried colorant coated food analog.

15. The method of claim 14 further comprising cutting the dried colorant coated food analog to produce colorant coated food analog pieces.

16. The method of claim 1 wherein the dough comprises from about 30% to 70% by weight of the meat slurry and from about 30% to about 70% by weight of the powder blend.

17. The method of claim 1 wherein the food analog has a moisture content of 12 wt. % to 19 wt. % and a water activity of 0.6 to 0.8.

18. The method of claim 1 wherein the shear mechanical energy of the extruding is from 275 kJ/kg to about 500 kJ/kg.

* * * * *